United States Patent [19]

Parsons

[11] Patent Number: 4,653,492
[45] Date of Patent: Mar. 31, 1987

[54] ELASTIC BANDAGE

[76] Inventor: Dorothy Parsons, 4643 Geneva North, Oakdale, Minn. 55109

[21] Appl. No.: 701,111

[22] Filed: Feb. 13, 1985

[51] Int. Cl.[4] .............................................. A61L 15/00
[52] U.S. Cl. ..................................... 128/155; 128/156
[58] Field of Search ............. 128/155, 156, 169, 87 R, 128/335

[56] References Cited

U.S. PATENT DOCUMENTS 2,018,517 10/1935 Fetter .................................. 128/155
2,698,270 12/1954 Mesek ............................. 128/156 X
2,811,154 10/1957 Scholl .................................. 128/156

Primary Examiner—Gregory E. McNeill
Attorney, Agent, or Firm—Jacobson and Johnson

[57] ABSTRACT

An elastic bandage having a resilient elastic layer and a relatively non-resilient layer to limit the stretching of the elastic layer so the bandage is not applied too tightly.

9 Claims, 6 Drawing Figures

ELASTIC BANDAGE

FIELD OF THE INVENTION

This invention relates generally to bandages and, more specifically, to improvements to elastic bandages.

BACKGROUND OF THE INVENTION

It is well known to wrap an elastic bandage around an injured extremity in order to apply a compressive force to the extremity. The compressive force helps control the swelling and also provides support. The difficulty with the application of elastic bandages is that to properly apply the bandage requires a certain amount of skill. If not applied properly, the bandage can be wound too tightly, which restricts circulation or if wound too loosely, does not provide the proper support or control of swelling. The present invention virtually eliminates the need for a skilled person to properly apply an elastic bandage.

DESCRIPTION OF THE PRIOR ART

The Quello U.S. Pat. No. 3,536,072 shows a laminated traction wrap strip having an outer layer of a spun bonded polyester and an inner layer of a polyester foam. Located on one surface is a pressure-sensitive adhesive for fastening the strip to the limb of a patient.

The Scholl U.S. Pat. No. 3,039,459 shows a multilayered adhesive traction bandage having a cushioned material to provide added cushioning properties.

The Wideman U.S. Pat. No. 3,842,832 shows an elastic wrap bandage which has an inner core of foam material and outer layers on opposite sides which are wrinkled to provide a nonslip surface. The outer layers also prevent overstretching the polyester core of the elastic bandage but do not prevent wrapping the bandage too tightly. Also, no mention is made of controlling the wrapping force on the elastic bandage with use of a second material.

The Kuhn U.S. Pat. No. 3,935,355 shows a multiple layer bandage which can be wrapped around a body before the bandage is eventually hardened.

The Patience U.S. Pat. No. 3,523,528 shows a compression bandage. Patience recognizes the problems in application of elastic bandages, i.e., if they are applied too loosely they do not stay in the same place or if applied too tightly, they must be loosened. The Patience solution is to incorporate special decay fibers in the bandage and then deliberately wrap the bandage *too tightly*. The decay properties of special fibers permit the compressive forces generated by the bandage to decrease and then remain constant thereafter.

BRIEF DESCRIPTION OF THE INVENTION

Briefly, the present invention of an elastic bandage comprises a layer of elastic material having sufficient resiliency so as to apply a compressive force to a body extremity when wrapped around the body extremity. Located proximate the elastic material is a second material which has either less resiliency or relatively little resiliency or no resiliency. The second material is characterized by having an elastic or elongation limit which is less than the elastic limit or elongation limit of the first layer of elastic material to thereby limit the stretching of the layer of elastic material so that an inexperienced person can apply the elastic bandage without fear of applying it too tightly or too loosely.

DESCRIPTION OF THE PREFERRED EMBODIMENT

Figure 1:
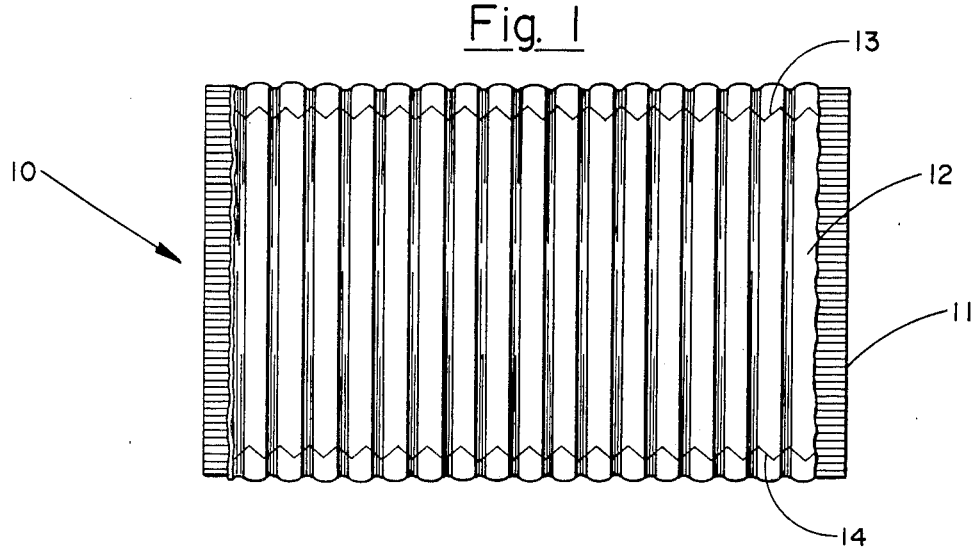
FIG. 1 is a plane view of my invention.

Referring to the drawings, reference numeral 10 generally identifies my elastic safety bandage which comprises an outer elastic member 11 and an inner member 12. Typically, outer member 11 is an elastic stretch material which is sold in a roll form as an elastic bandage for wrapping around body extremities to prevent swelling or to provide support. Elastic member 11 is shown attached to member 12 through a first zigzag stitch 13 and a second zigzag stitch 14 which are located near the edges of member 11. The purpose of the zigzag stitching is to permit the elastic member 11 and member 12 to stretch without distorting or breaking of threads 13 which hold the two members together. However, other means of fastening the members together could also be used and in some cases, it may not be necessary to even fasten the materials together. The material used in member 12 must be material that has less resiliency than the elastic member 11 or has very little or no resiliency yet when stretched, will act as a stop to prevent further stretching of member 11. I have found that crinkly cast padding sold by Johnson & Johnson under the name "Specialist Casting Padding" HRIA 137-009046 is a suitable material for member 12; however, other suitable materials would be usable therewith. The material used in elastic member 11 is the typical elastic bandage material having sufficient resiliency so as to apply a compressive force when wrapped around a body extremity. One such bandage is sold under the trademark ACE BANDAGE.

Figure 2:
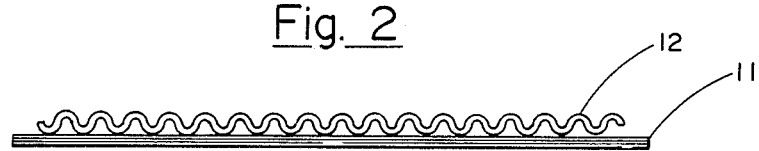
FIG. 2 is a side view showing my invention in the unstretched condition.
Figure 3:
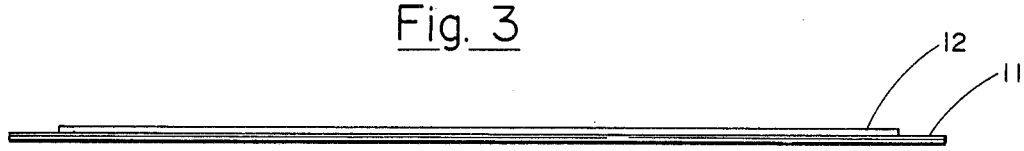
FIG. 3 is a side view showing the invention in the stretched condition.
Figure 4:
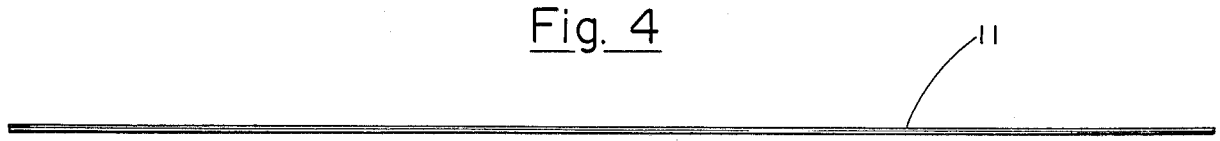
FIG. 4 shows the elastic portion of the invention in its stretched condition.

FIG. 2 shows a side view of my invention 10 in the unstretched condition with member 12 in a crinkled or unstretched condition. FIG. 3 illustrates how members 11 and 12 of bandage 10 can be stretched so that the crinkles are removed from member 12. In this condition member 12 prevents further stretching of elastic member 11. FIG. 4 shows only elastic member 11 in a stretched condition and illustrates how much further elastic member 11 could be stretched if it was not prevented from doing so by member 12.

Figure 5:
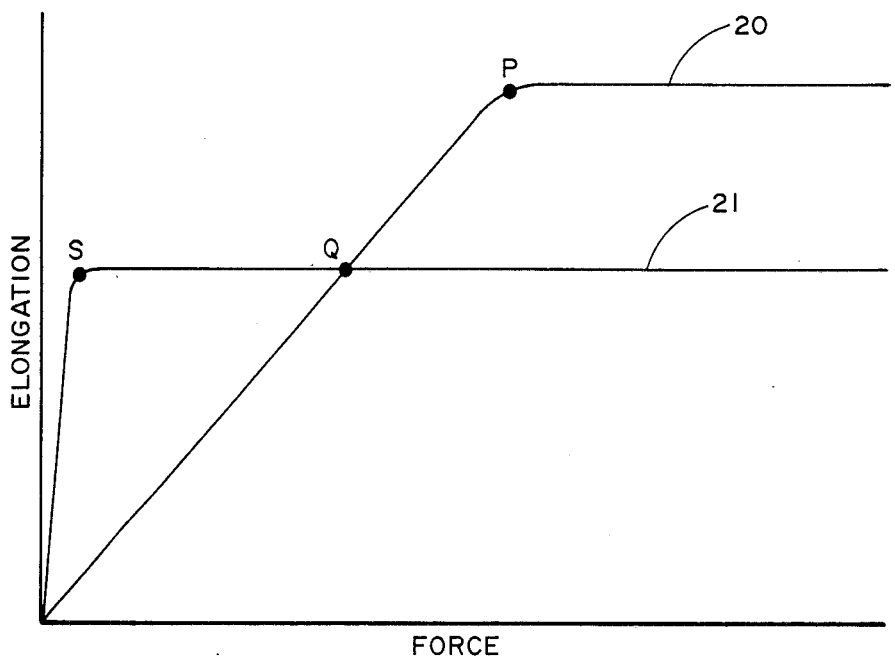
FIG. 5 shows a graph of elongation characteristics of the bandage materials.

In order to better understand the operation of my invention, reference should be made to FIG. 5 which shows a graph of elongation as a function of force for both elastic member 11 and member 12. Graph 20 shows that as the stretching force increases, there is a corresponding elongation of the elastic member 11 up to point P where elastic member 11 reaches its elastic limit or elongation limit. Beyond point P any increase in the stretching force does not produce any further elongation of elastic member 11. However, the inherent nature of elastic members used in elastic bandages is that if they are stretched to their elastic limit, they are too tight for most applications.

Reference numeral 21 shows the elongation of member 12 as a function of stretching force. Note the relatively small force required to stretch member 12 to its stretch limit(s) and that application of additional stretching force does not produce any further stretching of member 12. Thus, if member 11 and member 12 are sandwiched together, the member 12 with its lower stretch limit prevents elastic member 11 from reaching its stretch limit (P). Typically, the material used in member 12 is selected so that the intersection of curves 20 and 21 occur at a point Q where the composite elastic bandage is properly stretched, i.e., the proper amount of force produced by elastic bandage 10 occurs if bandage 10 had been stretched to the point indicated by Q. Thus, the purpose of member 12 is to act as a stop and *limit* the stretching of elastic member 11. By selecting the amount of stretch permitted in elastic member 11 by use of a flexible stop member 12, one can prevent an unskilled user from over-stretching or under-stretching the bandage and thus wrapping it too tightly or too loosely around a body extremity.

In some instances it is envisioned that member 12 could be sold as a separate item for laying on top of an elastic bandage. One would simultaneously stretch member 12 and the elastic bandage until member 12 would no longer stretch.

Figure 6:
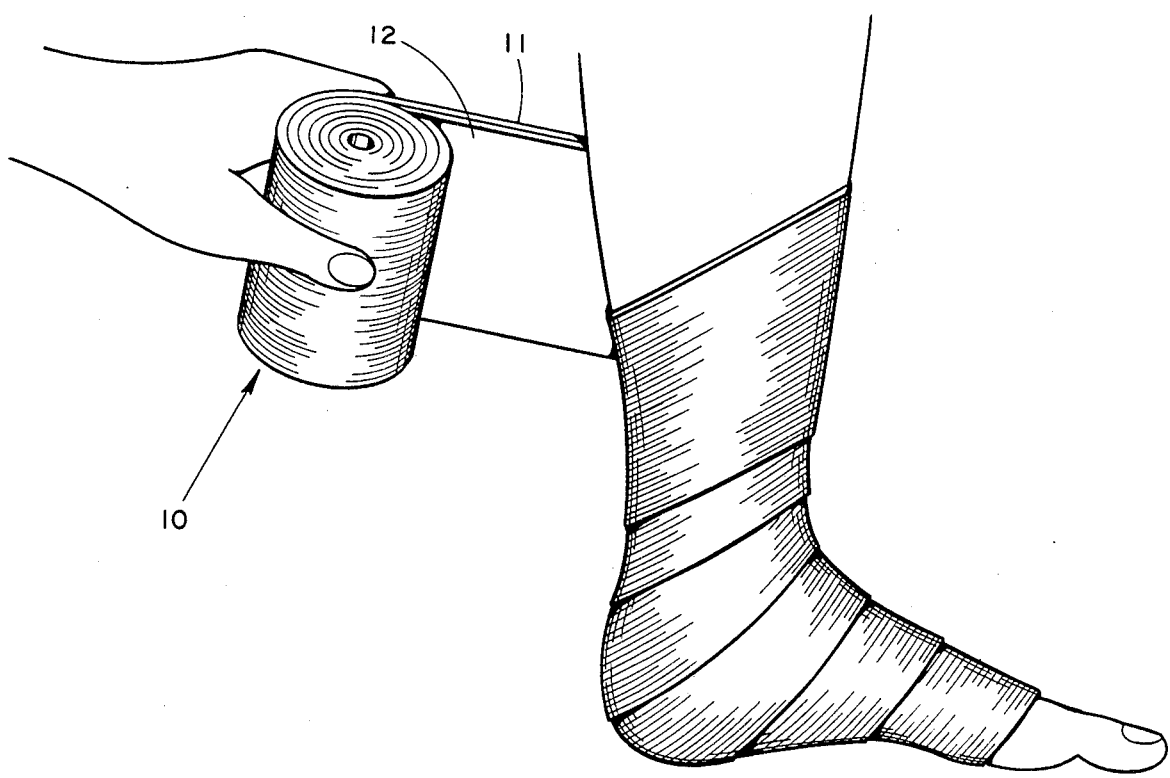
FIG. 6 shows my invention being applied to an ankle.

FIG. 6 illustrates how one can wrap my elastic bandage 10 around the user's ankle by stretching the bandage until the inner member 12 prevents any further stretching. Once this point is reached, an inexperienced user can wrap the bandage around the extremity without fear of wrapping the bandage too tightly or too loosely.

If crinkly padding is used, one can observe that if the crinkles are removed, the bandage is being applied properly. If other materials which leave no visual appearance are used, the feel or resistance of the bandage to further stretching can guide the user in applying the bandage.

I claim:

1. An elastic bandage for application to the extremity of a person or animal comprising:
   a stretchable resilient material, said stretchable resilient material having an elastic limit, said stretchable resilient material having sufficient resiliency so as to apply a compressive support force to an extremity when said stretchable resilient material is wrapped around the extremity; the improvement comprising a material located proximate to said stretchable resilient material; said material characterized by having an elongation limit substantially less than the elastic limit of said stretchable resilient material to thereby limit the stretching of said first stretchable resilient material to a predetermined amount so as to control the compressive force exerted to the extremity when the elastic bandage is wrapped around the extremity.

2. The invention of claim 1 wherein said stretchable resilient material and said material are fastened to each other by a stretchable fastener.

3. The invention of claim 2 wherein said stretchable fastener comprises a zigzag stitch.

4. The invention of claim 3 wherein said second material has ends and the zigzag stitching is located along the ends of said second material.

5. The invention of claim 1 wherein said second material comprises a fabric.

6. The invention of claim 5 wherein said stretching resilient material comprises an elastic strip of material.

7. The invention of claim 1 wherein said second material comprises a wrinkled material.

8. The method of applying an elastic bandage comprising the steps of:
   placing a stop member having an elongation limit adjacent to an elastic member having a greater elongation limit;
   stretching both members until the elongation limit of the stop member is reached; and
   wrapping the stretched members while in the stretching condition.

9. The method of claim 8 including the step of fastening the stop members to the elastic member.

* * * * *